(12) United States Patent
Kasahara et al.

(10) Patent No.: US 12,216,048 B2
(45) Date of Patent: Feb. 4, 2025

(54) MEASURING APPARATUS

(71) Applicants: Ryosuke Kasahara, Kanagawa (JP); Yoshio Wada, Kanagawa (JP); Yoshihiro Oba, Miyagi (JP); Toshihide Sasaki, Kanagawa (JP)

(72) Inventors: Ryosuke Kasahara, Kanagawa (JP); Yoshio Wada, Kanagawa (JP); Yoshihiro Oba, Miyagi (JP); Toshihide Sasaki, Kanagawa (JP)

(73) Assignee: RICOH COMPANY, LTD., Tokyo (JP)

( * ) Notice: Subject to any disclaimer, the term of this patent is extended or adjusted under 35 U.S.C. 154(b) by 121 days.

(21) Appl. No.: 18/014,756

(22) PCT Filed: Jul. 8, 2021

(86) PCT No.: PCT/IB2021/056110
§ 371 (c)(1),
(2) Date: Jan. 6, 2023

(87) PCT Pub. No.: WO2022/023846
PCT Pub. Date: Feb. 3, 2022

(65) Prior Publication Data
US 2023/0288323 A1  Sep. 14, 2023

(30) Foreign Application Priority Data

Jul. 30, 2020 (JP) .................................. 2020-129357
Jun. 3, 2021 (JP) .................................. 2021-093778

(51) Int. Cl.
G01N 21/59 (2006.01)
G01N 21/35 (2014.01)

(52) U.S. Cl.
CPC ..... *G01N 21/35* (2013.01); *G01N 2201/0634* (2013.01)

(58) Field of Classification Search
CPC . A61B 5/1455; A61B 5/14551; A61B 5/0059; A61B 5/00; A61B 2562/0238;
(Continued)

(56) References Cited

U.S. PATENT DOCUMENTS

2003/0160961 A1 * 8/2003 Hafeman ............. G01N 21/253
356/433
2004/0147034 A1 7/2004 Gore et al.
(Continued)

FOREIGN PATENT DOCUMENTS

JP  2010-217097  9/2010
JP  2012-132745  7/2012
(Continued)

OTHER PUBLICATIONS

International Search Report issued on Sep. 27, 2021 in PCT/IB2021/056110 filed on Jul. 8, 2021, 11 pages.
(Continued)

*Primary Examiner* — Don K Wong
(74) *Attorney, Agent, or Firm* — XSENSUS LLP

(57) ABSTRACT

A measuring apparatus includes a light source configured to emit light in a mid-infrared region, the light including: first-wavelength light having a wave number of from 970 $cm^{-1}$ or more to 1010 $cm^{-1}$ or less; and second-wavelength light different from the first-wavelength light, the second-wavelength light having a wave number of from 950 $cm^{-1}$ or more to 990 $cm^{-1}$ or less; a photosensor configured to detect the light emitted from the light source and reflected by a measurement target; and an information processing device configured to: obtain a first absorbance of the first-wavelength light and a second absorbance of the second-wavelength light from an output of the photosensor; and determine a biomarker of the measurement target based on the first absorbance and the second absorbance.

18 Claims, 15 Drawing Sheets

(58) Field of Classification Search
CPC .......... A61B 2562/0233; A61B 5/0086; G01N 21/359; G01N 21/35; G01N 21/00; G01N 2201/063; G01N 2201/062; G01N 2201/068; G01N 21/64
See application file for complete search history.

(56) References Cited

U.S. PATENT DOCUMENTS

| | | |
|---|---|---|
| 2016/0195473 A1 | 7/2016 | Fujiwara et al. |
| 2016/0360966 A1 | 12/2016 | Ishii et al. |
| 2017/0179682 A1 | 6/2017 | Ishii et al. |
| 2020/0170553 A1 | 6/2020 | Kasahara et al. |
| 2021/0259586 A1 | 8/2021 | Oba et al. |

FOREIGN PATENT DOCUMENTS

| | | |
|---|---|---|
| JP | 2017-140159 | 8/2017 |
| JP | 2019-037752 | 3/2019 |

OTHER PUBLICATIONS

Ryosuke Kasahara, et al., "Noninvasive glucose monitoring using mid-infrared absorption spectroscopy based on a few wavenumbers", Biomedical Optics Express, vol. 9, No. 1, Jan. 1, 2018 (Jan. 1, 2018), pp. 289-210.

* cited by examiner

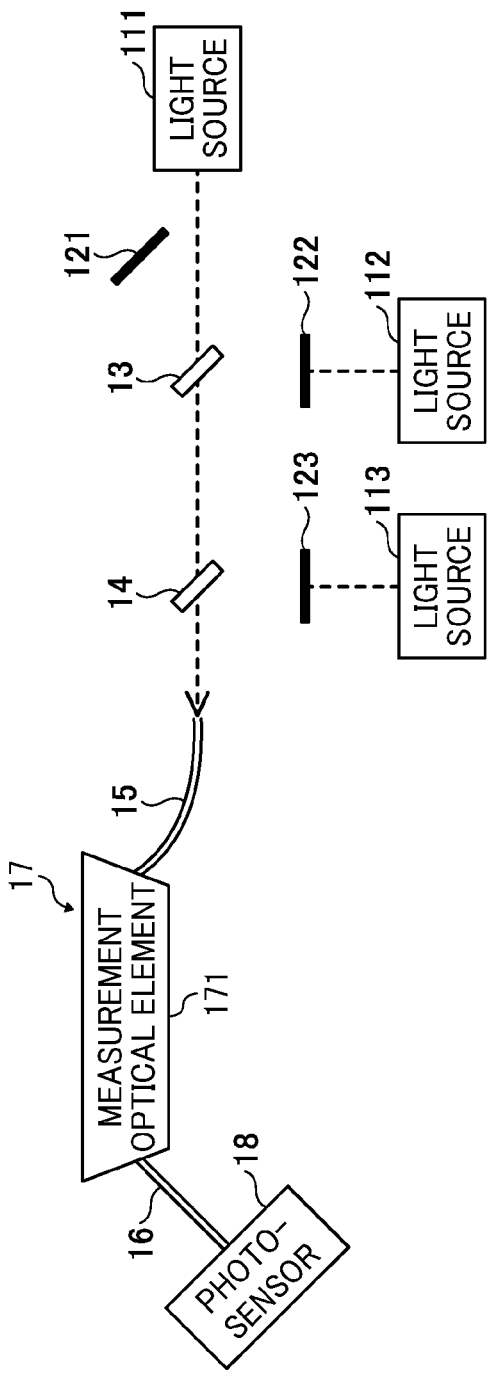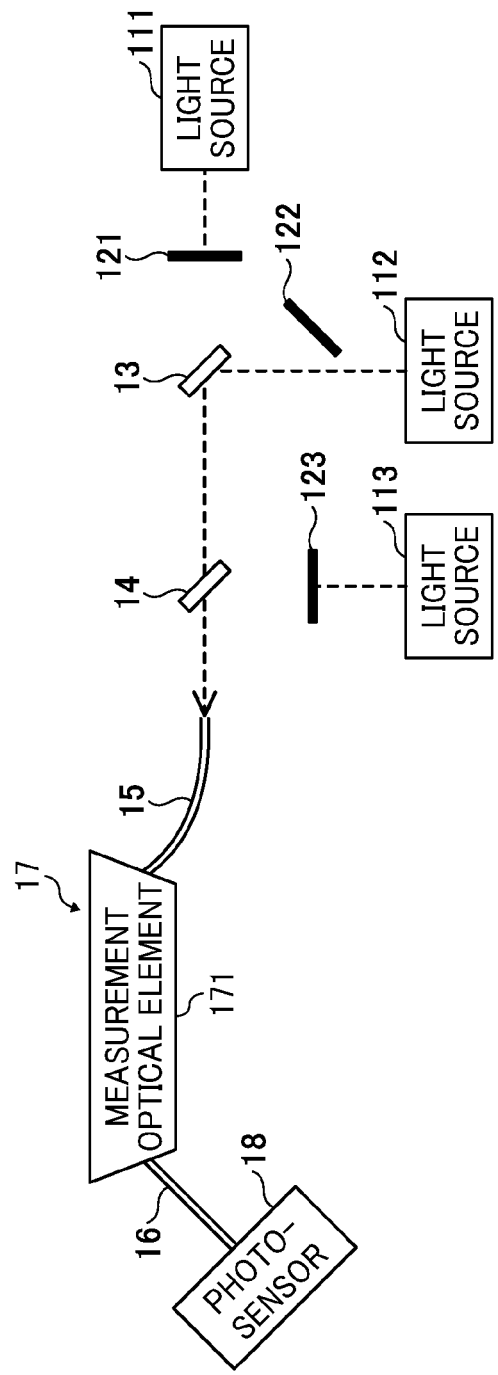

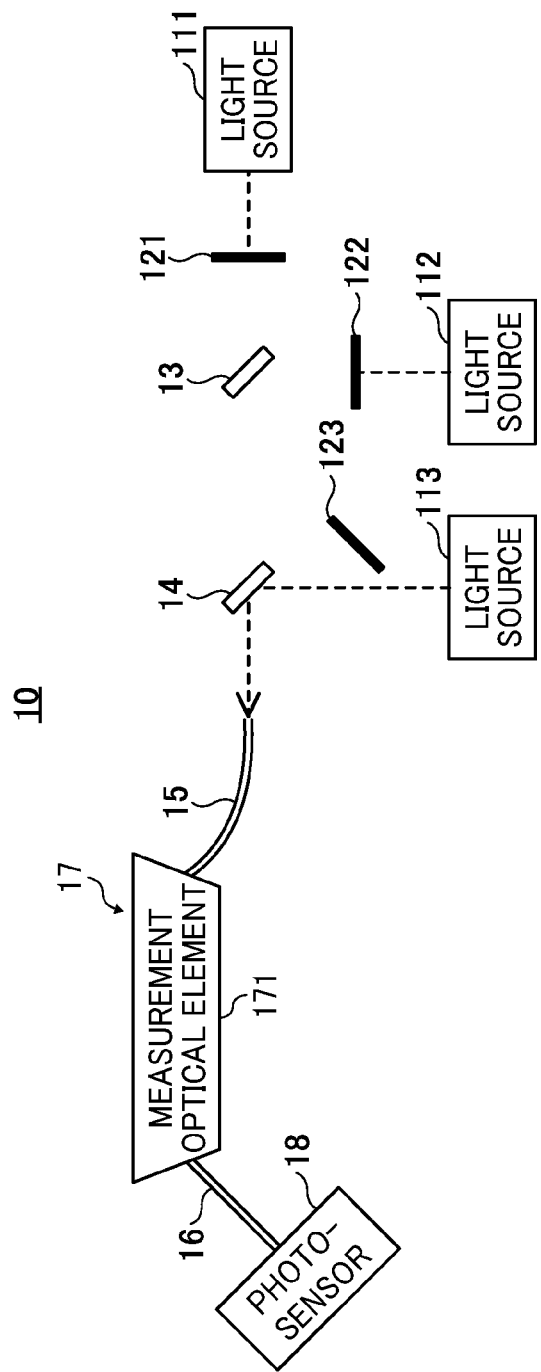

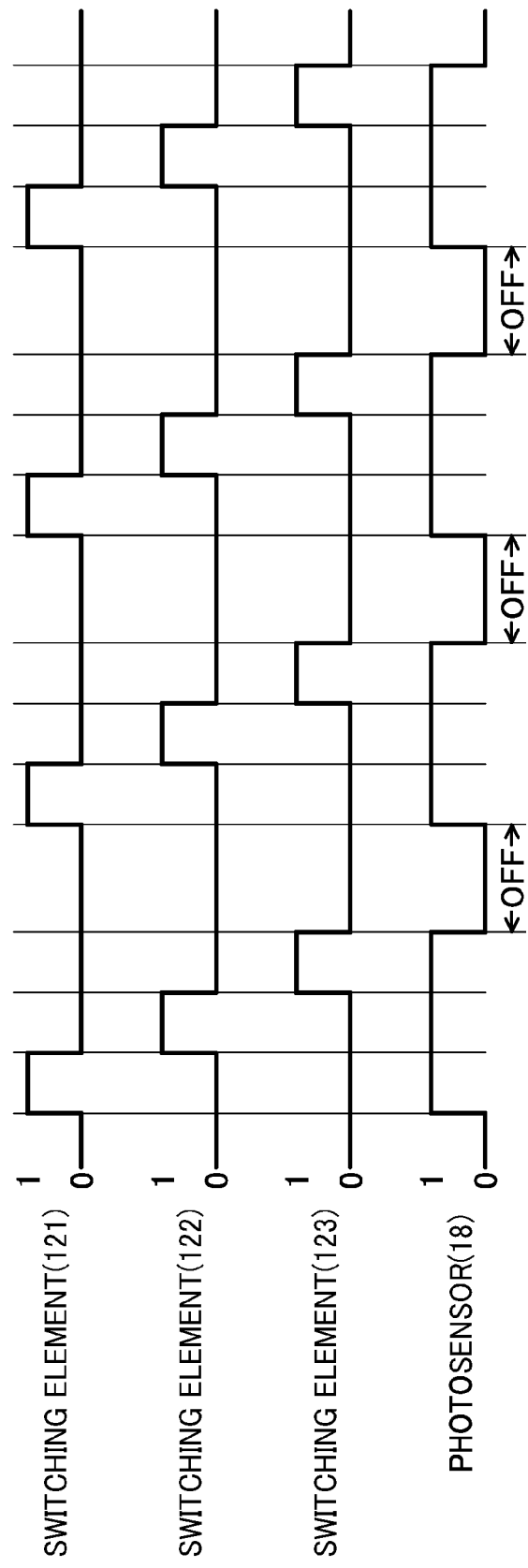

MEASURING APPARATUS

CROSS-REFERENCE TO RELATED APPLICATIONS

The present application is based on PCT filing PCT/IB2021/056110, filed Jul. 8, 2021, which claims priority to JP 2020-129357, filed Jul. 30, 2020, and JP 2021-093778, filed Jun. 3, 2021, the entire contents of each are incorporated herein by reference.

TECHNICAL FIELD

Embodiments of the present disclosure relate to a measuring apparatus for a biomarker.

BACKGROUND ART

In recent years, diabetic patients have increased all over the world, and noninvasive blood sugar level measurement without blood collection is desired. As a method of sensing using light, various methods such as a method using near-infrared light, a method using mid-infrared light, and a method using Raman spectroscopy have been proposed. Among those regions, the mid-infrared region corresponds to a fingerprint region in which the absorption of glucose is large, and the sensitivity of measurement can be higher than the near-infrared region. In addition to the blood glucose level, biomarkers such as hemoglobin concentration, blood lipids, blood proteins, and blood tumor DNA can be non-invasively measured in the mid-infrared region. In order to accurately measure glucose concentrations in the mid-infrared region, methods using light with wave numbers of 1035 $cm^{-1}$, 1080 $cm^{-1}$, and 1110 $cm^{-1}$ that reach absorption peaks of glucose have been proposed (for example, see Japanese Patent No. 5376439).

CITATION LIST

Patent Literature

[PTL 1]
Japanese Patent No. 5376439

SUMMARY OF INVENTION

Technical Problem

A typical measurement of biomarkers using mid-infrared light has difficulties in accurate and stable measurement because of the influence of individual differences in digestive absorption and metabolism over a period from before eating to after eating and differences in measurement environment.

It is an object of the present disclosure is to provide a non-invasive biomarker measuring apparatus with improved measurement stability and accuracy.

Solution to Problem

A measuring apparatus includes a light source configured to emit light in a mid-infrared region, the light including: first-wavelength light having a wave number of from 970 $cm^{-1}$ or more to 1010 $cm^{-1}$ or less; and second-wavelength light different from the first-wavelength light, the second-wavelength light having a wave number of from 950 $cm^{-1}$ or more to 990 $cm^{-1}$ or less; a photosensor configured to detect the light emitted from the light source and reflected by a measurement target; and an information processing device configured to: obtain a first absorbance of the first-wavelength light and a second absorbance of the second-wavelength light from an output of the photosensor; and determine a biomarker of the measurement target based on the first absorbance and the second absorbance.

Advantageous Effects of Invention

Some embodiments of the present disclosure provide a non-invasive biomarker measuring apparatus with improved measurement stability and accuracy.

BRIEF DESCRIPTION OF DRAWINGS

The accompanying drawings are intended to depict example embodiments of the present invention and should not be interpreted to limit the scope thereof. The accompanying drawings are not to be considered as drawn to scale unless explicitly noted. Also, identical or similar reference numerals designate identical or similar components throughout the several views.

FIG. 3 is an illustration of an operation of the measuring apparatus, according to an embodiment of the present disclosure.

FIG. 4 is an illustration of an operation of the measuring apparatus, according to another embodiment of the present disclosure.

FIG. 5 is an illustration of an operation of the measuring apparatus, according to still another embodiment of the present disclosure.

FIG. 6 is a timing chart of the control of the measuring apparatus.

DESCRIPTION OF EMBODIMENTS

Figure 1:
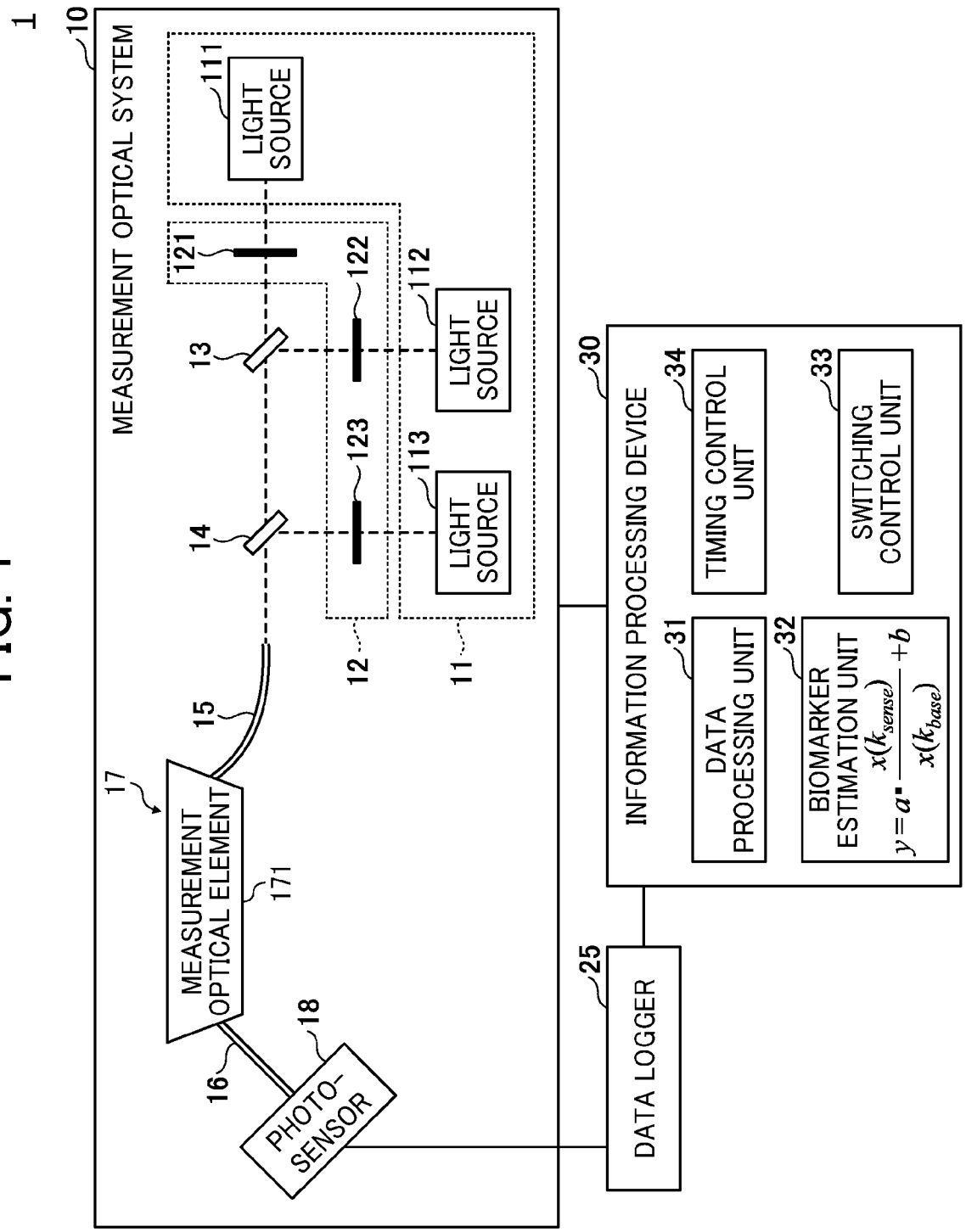
FIG. 1 is a schematic diagram of a measuring apparatus according to an embodiment.

The terminology used herein is for the purpose of describing particular embodiments only and is not intended to be limiting of the present invention. As used herein, the singular forms "a," "an," and "the" are intended to include the plural forms as well, unless the context clearly indicates otherwise.

In describing embodiments illustrated in the drawings, specific terminology is employed for the sake of clarity. However, the disclosure of this specification is not intended to be limited to the specific terminology so selected and it is to be understood that each specific element includes all technical equivalents that have a similar function, operate in a similar manner, and achieve a similar result.

In embodiments, a biomarker such as a blood glucose level is measured using at least two wavelengths included in a specific wave number range. In the field of infrared spectroscopy, the "wave number" is typically used. In the following description, the wave number is assumed to be synonymous with the wavelength as the wave number k is represented by the number of waves (1/X) per unit length.

At least one of two or more wavelengths may be used to normalize measurement data obtained by the measurement optical system. Using the normalized wavelength, a continuously-fluctuating measurement state, which refers to variations in a contact state of a measurement optical element with an area (i.e., measurement site) of a body to be measured, can be corrected.

To obtain stable measurement results irrespective of an individual difference, an appropriate range to select two or more wavelengths is determined. Specifically, measurement datasets in the mid-infrared region are collected over a wide range of subjects, different meal contents, and different measurement times, and an appropriate wavelength range is determined from the correlation between the collected data sets and the transition of a typical biomarker during a period from before eating to after eating.

For a blood glucose level, for example, the transition of a typical biomarker is a series of changes in which the blood glucose level is low before eating, peaks at 40 minutes after eating, and then returns to before eating at 180 minutes after eating. Two or more wavelengths used for measurement are selected from a wavelength range in which the correlation between the collected data and the typical transition is high. This enables a stable and accurate non-invasive measurement of a biomarker regardless of individual differences.

FIG. 1 is a schematic diagram of a measuring apparatus 1 according to an embodiment of the present disclosure. The measuring apparatus 1 includes a measurement optical system 10 and an information processing device 30. In FIG. 1, a data logger 25 that records data is disposed between the measurement optical system 10 and the information processing device 30. In some examples, the measurement result obtained by the measurement optical system 10 is directly input to the information processing device 30.

The measurement optical system 10 includes a light source device 11, a switch 12, a measurement optical element 17, and a photosensor 18. Depending on the design and arrangement of the optical path, optical elements such as optical multiplexers/demultiplexers 13 and 14 are between the light source device 11 and the measurement optical element 17. As the optical multiplexers/demultiplexers 13 and 14, a dichroic prism, a semi-reflective mirror, or a polarization beam splitter/combiner is used. A light-guide member 15 or 16 is connected to at least one of the incident side and the exit side of the measurement optical element 17. Examples of the light-guide member 15 or 16 include an optical fiber and an optical mirror. An optical path from each light source to the light-guide member 15 is indicated by a broken line within the measurement optical system 10.

The light source device 11 outputs light having at least two wavelengths selected from a specific wave number range. The specific wave number range is determined in advance to allow a stable measurement of a biomarker irrespective of the individual differences or the difference in the measurement state. The determination of the wave number range is described later.

In the example of FIG. 1, three light sources 111, 112, and 113 that output light beams having different wavelengths are used. However, no limitation is intended therein. As the light source device 11, a single wavelength variable light source or a light source that emits light over a wide wavelength range is used. Examples of such a light source with a wide-wavelength range include a lamp light source, a light emitting diode (LED), and a super luminescent diode (SLD). The same measurement can be performed by using a combination of an infrared lamp in a wide wavelength range and a wavelength filter or a combination of an infrared lamp in a wide wavelength range and a spectrometer such as a Fourier transform infrared spectrometer (FTIR).

When a light source in a wide wavelength range is used, a wavelength filter for extracting a desired wavelength is provided on the exit side of the light source device 11 as needed. Alternatively, multiple light receiving elements may be used for the photosensor 18, and a wavelength filter may be disposed on the incident side of each light receiving element. The number of wavelengths used for the measurement is not limited to three, and, in some examples, is two, or four or more. In some examples, when individual light sources 111, 112, 113 are used, a portion of the output light of each light source is monitored to correct its output fluctuation.

The switch 12 switches the wavelength of light incident on the measurement optical element 17. In the example of FIG. 1, switching elements 121, 122, and 123 are provided on the exit sides of the light sources 111, 112, and 113, respectively. In some examples, the light sources 111, 112, and 113 each are controlled for on/off. When one wavelength-variable light source is used, the switch 12 serves as a selector for selecting a wavelength of a light source.

The switch 12 has any configuration that is capable of changing the wavelength of light emitted to the area to be measured. In some examples, one or more shutters are used to selectively block light emitted from the light sources 111, 112, and 113. In some other examples, one or more switches are used to switch on/off of the light sources 111, 112, and 113.

The light having the wavelength selected by the switch 12 is guided to the measurement optical element 17 through the optical multiplexers/demultiplexers 13 and 14 or the light-guide member 15 as needed. The measurement optical element 17 has a contact surface 171 with the object to be measured (i.e., a measurement target). During the measurement, the contact surface 171 of the measurement optical element 17 is pressed against the object to be measured and receives light returned from the measurement site, that is, light absorbed by the measurement site.

The light incident on the measurement optical element 17 undergoes attenuation corresponding to the light absorption spectrum of the medium to be measured at the interface between the measurement site and the contact surface 171. The attenuated light emitted from the measurement optical element 17 contains information inside the medium to be measured. In some examples for non-invasive measurement using light in the mid-infrared region, an attenuated total reflection (ATR) prism is used as the measurement optical element 17. The ATR prism is suitable for spectroscopy in the mid-infrared region where light absorption of glucose or glycogen is observed.

The ATR method utilizes penetration or seepage of light, which occurs when infrared light incident on the ATR prism having a high refractive index is totally reflected at an interface between the prism and a medium to be measured. The field (i.e., an evanescent field) generated by such a penetration of light is absorbed by the object to be measured when the ATR prism is pressed against the object to be measured.

The infrared light seeps into the measurement site from the ATR prism by a depth of approximately several microns, and fails to reach capillaries at a depth of approximately several hundred microns. However, it is known that components such as blood plasma in blood vessels ooze as tissue fluid (interstitial fluid) into skin and mucosal cells. The biomarker can be measured by detecting a component such as glucose in the tissue fluid as an intensity or absorbance of the light absorption spectrum.

Such a measurement of an intensity or absorbance of the light absorption spectrum using the light seepage at the boundary is suitable for a measurement site such as an oral mucosa having no epidermis, an earlobe or a lip, whose epidermis is thin.

The light emitted from the measurement optical element 17 is detected by the photosensor 18 as an optical signal including information. When the light-guide member 16 is used, the optical signal from the measurement optical element 17 is received by the photosensor 18 after passing through the light-guide member 16. The photosensor 18 converts the received optical signal into an electrical signal and outputs the electrical signal to the data logger 25. The information recorded by the data logger 25 is transmitted to the information processing device 30 and undergoes data processing to estimate a target biomarker. As described above, in some examples, the information processing device 30 has the capability of the data logger 25.

In the example of FIG. 1 that uses an output of a single photosensor 18, a signal output from the photosensor 18 is processed in synchronization with the switching timing of the switching elements 121 to 123. This enables an appropriate measurement of absorbances for different wavelengths using a single photosensor 18.

The information processing device 30 includes a data processing unit 31, a biomarker estimation unit 32, a switching control unit 33, and a timing control unit 34, which are functional blocks. The data processing unit 31 obtains an absorbance of the object to be measured for each wavelength from the light intensity of each wavelength detected by the photosensor 18. The absorbance A at a wave number k is given by formula (1) below:

$$A(k) = -\log_{10}(I/I_0) \quad (1)$$

where $I_0$ is an intensity of light incident on the measurement optical element 17, that is, the intensity of light emitted from the light source device 11, and I is the intensity of light detected by the photosensor 18 after being emitted from the measurement optical element 17.

The biomarker estimation unit 32 estimates a biomarker based on the absorbance of each wavelength using a prediction formula to be described later. The switching control unit 33 controls the operation of the switch 12 of the measurement optical system 10. The timing control unit 34 controls the timing of recording and capturing the detection result of the photosensor 18 in synchronization with the switching of the wavelength. In some examples, the switching control unit 33 is provided outside the information processing device 30.

In this case, an external switching control unit and the information processing device 30 is connected by a cable or wirelessly, and the switching control for the measurement optical system 10 and the data acquisition in the information processing device 30 are synchronized.

In at least one embodiment, two or more wavelengths suitable for estimating a biomarker are set for the measuring apparatus 1, and the biomarker estimation unit 32 stably and accurately estimates the biomarker based on the absorbances at the two or more wavelengths.

Figure 2:
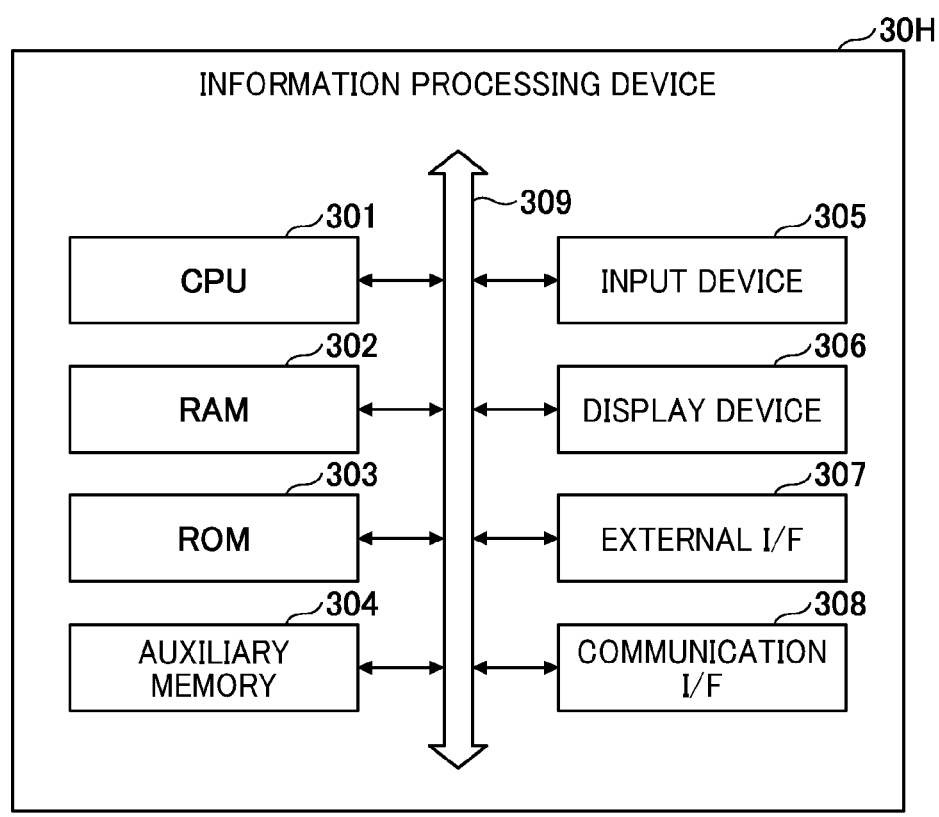
FIG. 2 is a block diagram of a hardware configuration of an information processing device.

FIG. 2 is a block diagram of a hardware configuration of an information processing device 30H. The information processing device 30H includes a hardware configuration that implements the capability of the information processing device 30 in FIG. 1. The information processing device 30H includes a central processing unit (CPU) 301, a random access memory (RAM) 302, a read only memory (ROM) 303, an auxiliary memory 304, an input device 305, a display device 306, an external interface (I/F) 307, and a communication interface (I/F) 308, which are connected to each other via a bus 309.

In some examples, the CPU 301, the RAM 302 as a main storage, and the ROM 303 are directly connected to the main bus, and other devices are connected to the main bus via an internal interface. In FIG. 2, all the devices are depicted as being connected to each other by the bus 309.

The data processing unit 31, the biomarker estimation unit 32, the switching control unit 33, and the timing control unit 34 in FIG. 1 are implemented by the CPU 301, the RAM 302, and ROM 303. In some examples, the information processing device 30H further includes an application specific integrated circuit (ASIC) with a built-in memory or a programmable logic device (PLD), which are separate from the CPU 301, and the functions of the switching control unit 33 and the timing control unit 34 are shared by the ASIC or the PLD.

The ROM 303 stores programs and parameters according to which the CPU 301 executes processing. In some examples, the prediction formula used for estimating the biomarker is stored in the ROM 303. The RAM 302 serves as a work area for arithmetic processing by the CPU 31.

The date transmitted from the data logger 25 and the biomarker estimated by the CPU 31 are recorded in the ROM 303 or in the auxiliary memory 304.

The input device is a user interface such as a touch panel and a keyboard. The display device 306 displays the data processing result of and the biomarker estimated by the CPU 31. The external I/F 307 is used to connect the information processing device 30H to the data logger 25 and the light source device 11 and the switch 12 of the measurement optical system 10.

The communication I/F 308 is used for data communication with a network or an external server. In some examples, the biomarker estimated by the CPU 31 is transmitted to a subject to be measured via a network or an external server.

FIGS. 3, 4, and 5 are illustrations of operation examples of the measurement optical system 10. In the example of FIG. 3, light having a first wavelengths (i.e., first-wavelength light) emitted from the light source 111 is selected. In some examples where the switching elements 121 to 123 are shutters, the CPU 301 opens the switching element 121 and closes the switching elements 122 and 123 to guide only the light emitted from the light source 111 to the measurement optical element 17. In some other examples where the switching elements 121 to 123 are on/off switches (or current-injection switches) of the light sources 111 to 113, the CPU 301 turns on the light source 111 and turns off the light source 112 and the light source 113 to cause the light source 111 to emit light having the first wavelength.

The light having the first wavelength passes through the optical multiplexers/demultiplexers 13 and 14 and the light-guide member 15 and is incident on the measurement optical element 17. As described above, the measurement optical element 17 has the contact surface 171 pressed against the measurement site of the object to be measured, and a signal corresponding to the light having the first wavelength that has been attenuated at the measurement site is detected by the photosensor 18 after passing through the light-guide member 16.

In the example of FIG. 4, light having a second wavelength (i.e., second-wavelength light) emitted from the light source 112 is selected. In some examples where the switching elements 121 to 123 are shutters, the CPU 301 opens the switching element 122 and closes the switching elements 121 and 123 to guide only the light emitted from the light source 112 to the measurement optical element 17. In some other examples where the switching elements 121 to 123 are on/off switches (or current-injection switches) of the light sources 111 to 113, the CPU 301 turns on the light source 112 and turns off the light source 111 and the light source 113 to cause the light source 112 to emit light having the second wavelength.

The light having the second wavelength passes through the optical multiplexers/demultiplexers 13 and 14 and the light-guide member 15 and is incident on the measurement optical element 17. The signal corresponding to the light having the second wavelength that has been attenuated at the interface between the measurement optical element 17 and the object to be measured is detected by the photosensor 18 after passing through the light-guide member 16.

In the example of FIG. 5, light having a third wavelength (i.e., third-wavelength light) emitted from the light source 113 is selected. In some examples where the switching elements 121 to 123 are shutters, the CPU 301 opens the switching element 123 and closes the switching elements 121 and 122 to guide only the light emitted from the light source 113 to the measurement optical element 17. In some other examples where the switching elements 121 to 123 are on/off switches (or current-injection switches) of the light sources 111 to 113, the CPU 301 turns on the light source 113 and turns off the light source 111 and the light source 112 to cause the light source 113 to emit light having the third wavelength.

The light having the third wavelength passes through the optical multiplexers/demultiplexers 13 and 14 and the light-guide member 15 and is incident on the measurement optical element 17. The signal corresponding to the light having the third wavelength that has been attenuated at the interface between the measurement optical element 17 and the object to be measured is detected by the photosensor 18 after passing through the light-guide member 16. In such manners, the light absorption spectrum intensity at the object to be measured with respect to light of each wavelength is detected.

FIG. 6 is a timing chart of the control of the measuring apparatus 1, according to an embodiment of the present disclosure.

The operation timings of the switching elements 121, 122, and 123 and the incoming timing at the photosensor 18 are indicated on the time axis. A value "1" on the vertical axis indicates a state in which the object to be measured is irradiated with light, that is, a state in which the shutter is open, or the light source is turned on. The value "0" indicates a state in which no light is emitted from the light source, that is, a state in which the shutter is closed, or the light source is turned off.

When the switching element 121 is open, and the switching elements 122 and 123 are closed, the measuring light having the first wavelength comes into the photosensor 18. When the switching element 122 is open, and the switching elements 121 and 123 are closed, the measuring light having the second wavelength comes into the photosensor 18. When the switching element 123 is open, and the switching elements 121 and 122 are closed, the measuring light having the third wavelength comes into the photosensor 18.

When all of the switching elements 121 to 123 are closed (i.e, the OFF sections in FIG. 6), the measuring light does not comes into the photosensor 18, but background light, that is, light returned from the object that is being measured, or light emitted from the measurement optical system 10 is detected by the photosensor 18.

The detection results of the photosensor 18 when all the switching elements 121 to 123 are closed are stored in the data processing unit 31 as a correction value, and the measurement results for the wavelengths obtained at near time are corrected. For example, the correction value is subtracted from each of the intensities of received measuring light beams of three wavelengths. This correction eliminates the influences of the characteristic fluctuation due to the change in the ambient temperature or the temperature of the object to be measured, the sensitivity fluctuation of the photosensor 18 due to the temperature change, and the radiation light from the object to be measured (object that is being measured) or the measuring device.

Notably, in some examples, different correction values are used to correct the measurement results for the three wavelengths obtained in one switching cycle. For example, a correction value obtained in a certain OFF interval is applied to the detection results of two wavelengths obtained immediately before the OFF interval and the detection result of one wavelength obtained immediately after the OFF interval. This reduces the time lag between the measurement of the background light and the correction of the measurement results using the measured background light.

Notably, the correction may not be performed after the measurement results of the three wavelengths are acquired. For example, the measurement and the correction of the measurement result are repeated in the following order: measurement of light having the first wavelength (i.e., a first measurement result); measurement of background light and correction of the first measurement result using the measured background light; measurement of light having the second wavelength (i.e., a second measurement result); measurement of background light and correction of the second measurement result using the measured background light; measurement of light having the third wavelength (i.e., a third measurement result); measurement of background light and correction of the third measurement result using the measured background light, where the OFF interval is provided between the measurements for the respectively wavelengths. This method enables a correction of a detection value for each measurement wavelength, using a correction value obtained at a time closest to the time of measurement of each measuring light.

Notably, switching the detection interval (an interval of value "1") and the OFF interval (an interval of value "0") of the photosensor 18 at short intervals can effectively eliminate the influences of disturbance. Further, the contact state between the measurement optical element 17 and the measurement site might change during the measurement, and the obtained absorbance might fluctuate accordingly. Such an issue is dealt with by providing the OFF sections at short intervals to eliminate or reduce the fluctuations in absorbance due to changes in the contact state and thus increase the accuracy of measurement.

In some examples, prior to the actual measurement, the output intensities of the light sources 111, 112, and 113 each are changed in stages. The linearity of the photosensor 18 is corrected by checking a change in the intensity of light received at the photosensor 18 according to a change in the output intensity of the light source. In a very short time in which no change in the measurement target or the measurement environment is observed, the output intensity of the light source and the intensity of light received at the photosensor 18 are to be linearly proportional to each other. However, when the linearity of the photosensor 18 is poor, a region occurs where the output intensity of the light source and the intensity of light received at the photosensor 18 deviate from the linear proportion. In this case, the influence of such a non-linearity of the photosensor 18 is eliminated by using preliminarily obtained data for the region where the linearity of the photosensor 18 is good, and the linear proportion between the linearity of the photosensor 18 and the intensity of light received at the photosensor 18 is observed.

Next, an appropriate wavelength range used for measurement of biomarkers is described. In an embodiment, wavelengths selected from the following wavelength ranges are used: (A) a first wavelength selected from the range of wave numbers of from 970 $cm^{-1}$ or more to 1010 $cm^{-1}$ or less, and a second wavelength selected from the range of wave numbers of from 950 $cm^{-1}$ or more to 990 $cm^{-1}$ or less; (B) two wavelengths selected from the range of wave number of from 1130 $cm^{-1}$ or more to 1220 $cm^{-1}$ or less. In particular, the correlation increases with a combination of the first wavelength in the range of wave number of from 1156 $cm^{-1}$ to 1164 $cm^{-1}$ and the second wavelength in the range of wave number of from 1164 $cm^{-1}$ to 1174 $cm^{-1}$ or a combination of the first wavelength in the range of wave number of from 1134 $cm^{-1}$ to 1146 $cm^{-1}$ and the second wavelength in the range of wave number of from 1170 $cm^{-1}$ to 1216 $cm^{-1}$; and (C) two wavelengths selected from the range of wave numbers of from 1700 $cm^{-1}$ or more to 1760 $cm^{-1}$ or less.

In examples using the wavelength range (A), a biomarker is estimated from the absorbance at the first wavelength selected from at least the range of from 970 $cm^{-1}$ or more to 1010 $cm^{-1}$ or less, and the absorbance at the second wavelength selected from the range of from 950 $cm^{-1}$ or more to 990 $cm^{-1}$ or less.

In examples using the wavelength range (B), a biomarker is estimated from the absorbances at the two wavelengths selected from the range of from 1130 $cm^{-1}$ or more to 1220 $cm^{-1}$ or less. In this case, the accuracy of estimation increases by using the absorbances for light having the first wavelength in the range of wave number of from 1156 $cm^{-1}$ to 1164 $cm^{-1}$ and light having the second wavelength in the range of wave number of from 1164 $cm^{-1}$ to 1174 $cm^{-1}$ or the absorbances for light having the first wavelength in the range of wave number of from 1134 $cm^{-1}$ to 1146 $cm^{-1}$ and light having the second wavelength in the range of wave number of from 1170 $cm^{-1}$ to 1216 $cm^{-1}$.

In examples using the wavelength range (C), a biomarker is estimated from the absorbances at the two wavelengths selected from the range of from 1700 $cm^{-1}$ or more to 1760 $cm^{-1}$ or less.

Notably, two or more wavelengths are selected from not only one of the wavelength ranges (A) to (C) but also a combination selected from two or more of the wavelength ranges (A) to (C). The following describes the validity of these wavelength ranges by taking the blood sugar level (glucose) as an example of the biomarker.

In an embodiment, a blood glucose level is accurately and stably measured irrespective of individual differences in metabolism over a period from before eating to after eating and differences in measurement environment. First, in order to reduce variations in measurement results due to individual differences, measurement results of blood glucose levels are collected from multiple subjects with different contents of the meal over a wide time range from 100 minutes before eating to 250 minutes after eating. A correlation between the obtained measurement results and a typical transition of a blood glucose level, which is low before eating, reaches its peak 40 minutes after eating, and then returns to the level of before eating 180 minutes after eating, is obtained, and a wavelength range in which the correlation becomes high is determined.

Further, prediction formula (2) below is used to reduce the influences of the variations in the contact state of the measurement optical element 17 (e.g., an ATR prism) and the measurement site:

$$y = a \times x(\text{sense})/x(\text{base}) + b \quad (2)$$

where y is a blood glucose level estimated from the measurement results of the photosensor 18, x(sense) is an absorbance at a sense wavelength sensitive to molecules contained in glucose, and x(base) is an absorbance at a base wavelength for normalizing the contact state of the ATR prism. The x(sense) and the x(base) correspond to the absorbance A(k) in formula (1). In the prediction formula (2), "a" and "b" are coefficients of a linear expression for obtaining the blood glucose value y from the absorbance ratio (x(sense)/x(base)) to correct the sensitivity. In some examples, the coefficients "a" and the coefficient "b" are updated by learning in the process of data collection and actual measurement because the coefficients "a" and "b" depend on individual differences between apparatuses or persons. For example, when the sense wavelength is 980 $cm^{-1}$, and the base wavelength is 986 $cm^{-1}$, a is −1900, and b is 2000.

Using a value obtained by dividing the absorbance measured at the sense wavelength by the absorbance at the base wavelength serving as a reference enables a correction of variations in the contact state that varies for each measurement. In this case, the base wavelength and the sense wavelength are not distinguished from each other to determine the wavelength range, and the wavelengths referred to as the base wavelength and the sense wavelength for convenience. In some examples of the actual measurement, however, the detected base wavelength is set as the absorption wavelength of the object to be measured, and the sense wavelength is set as the reference wavelength. In other words, it is effective even if the detected base wavelength and sense wavelength are reversed.

For example, the lips as a measurement site undergoes the measurement to obtain the light absorption spectrum intensity of the lips. A lamp of a Fourier transform infrared spectrometer is used as a light source to measure a light absorption spectrum intensity of the lips for each wavelength.

Using the prediction formula (2) described above, a correlation with a typical transition of the blood glucose level over a period from before eating to after eating is obtained where a period from before eating to after eating for each meal is defined as one cycle. Further, multiple subjects with different multiple contents of the meal undergo measurement of the blood glucose levels at any desired timing during a period from 100 minutes before eating to 250 minutes after eating.

Figure 7:
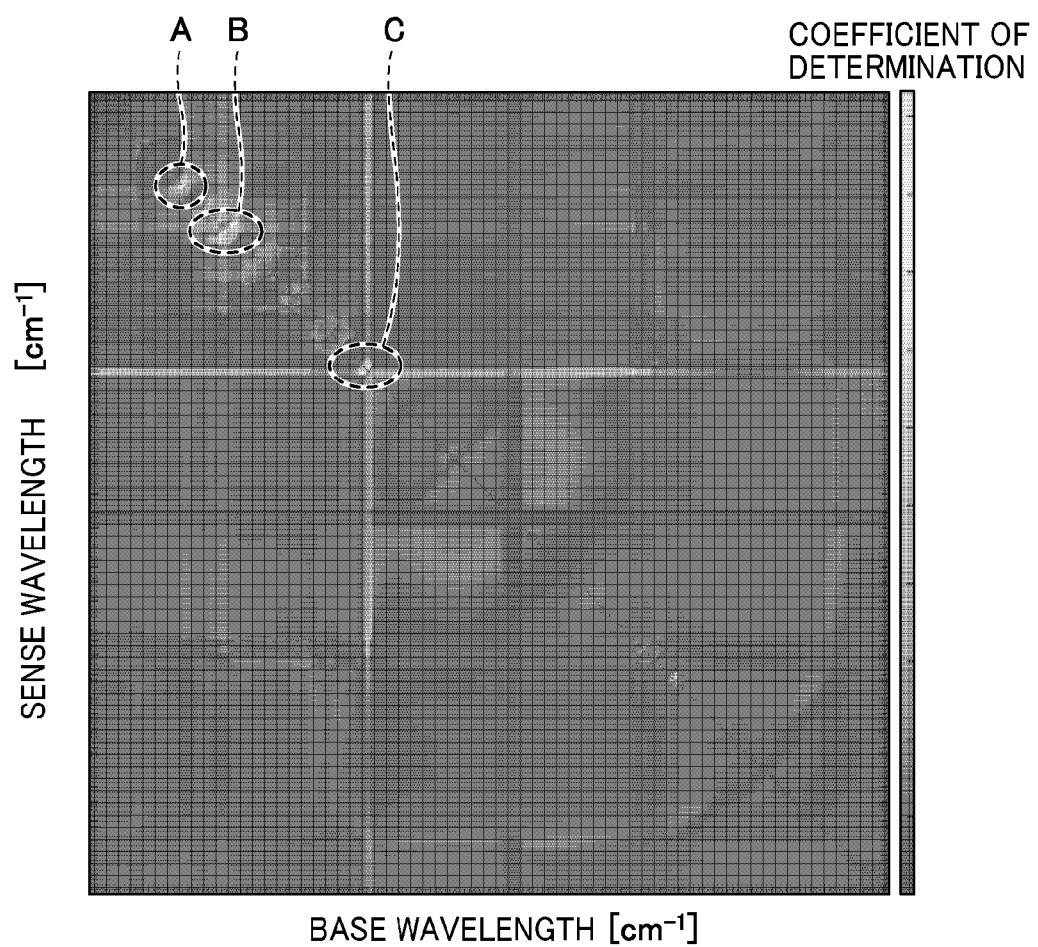
FIG. 7 is a diagram in which the average values of the coefficients of determination are mapped to the sense wavelength and the base wavelength.

FIG. 7 is a map diagram of the coefficients of determination obtained for one cycle, which are mapped to the sense wavelength (i.e., a first wavelength) and the base wavelength (i.e., a second wavelength). The horizontal axis represents the base wavelength, the vertical axis on the left represents the sense wavelength, and the vertical axis on the right represents the coefficient of determination. The coefficient of determination serves as an index representing the prediction accuracy represented by the mean value of the square of the correlation coefficient R. The correlation refers to a correlation between a blood glucose level before and after eating the meal obtained from each person and the typical transition as described above.

In the map diagram of FIG. 7, the correlation increases as the color saturation decreases. The regions A, B, and C having high correlation are indicated by circles. The region A is for a combination of the sense wavelength of 970±20 $cm^{-1}$ (i.e., in the range of wave number of from 950 $cm^{-1}$ or more to 990 $cm^{-1}$ or less) and the base wavelength of 990±20 $cm^{-1}$ (i.e., in the range of wave number of from 970 $cm^{-1}$ or more to 1010 $cm^{-1}$ or less) or vice versa. The region A represents the validity of the wavelength range (A).

The region B is for a combination of the first wavelength and the second wavelength selected from the range of wave number of from 1130 $cm^{-1}$ to 1220 $cm^{-1}$. As will be described later, in the region B, two areas of two combinations of the wavelengths, in which the correlation becomes particularly high, are observed within the range from 1130 $cm^{-1}$ to 1220 $cm^{-1}$. The region B represents the validity of the wavelength range (B).

The region C is for a combination of the sense wavelength in the range of wave number of from 1700 $cm^{-1}$ to 1760 $cm^{-1}$ and the base wavelength in the range of wave number of from 1700 $cm^{-1}$ to 1760 $cm^{-1}$. The region C represents the validity of the wavelength range (C).

Figure 8:
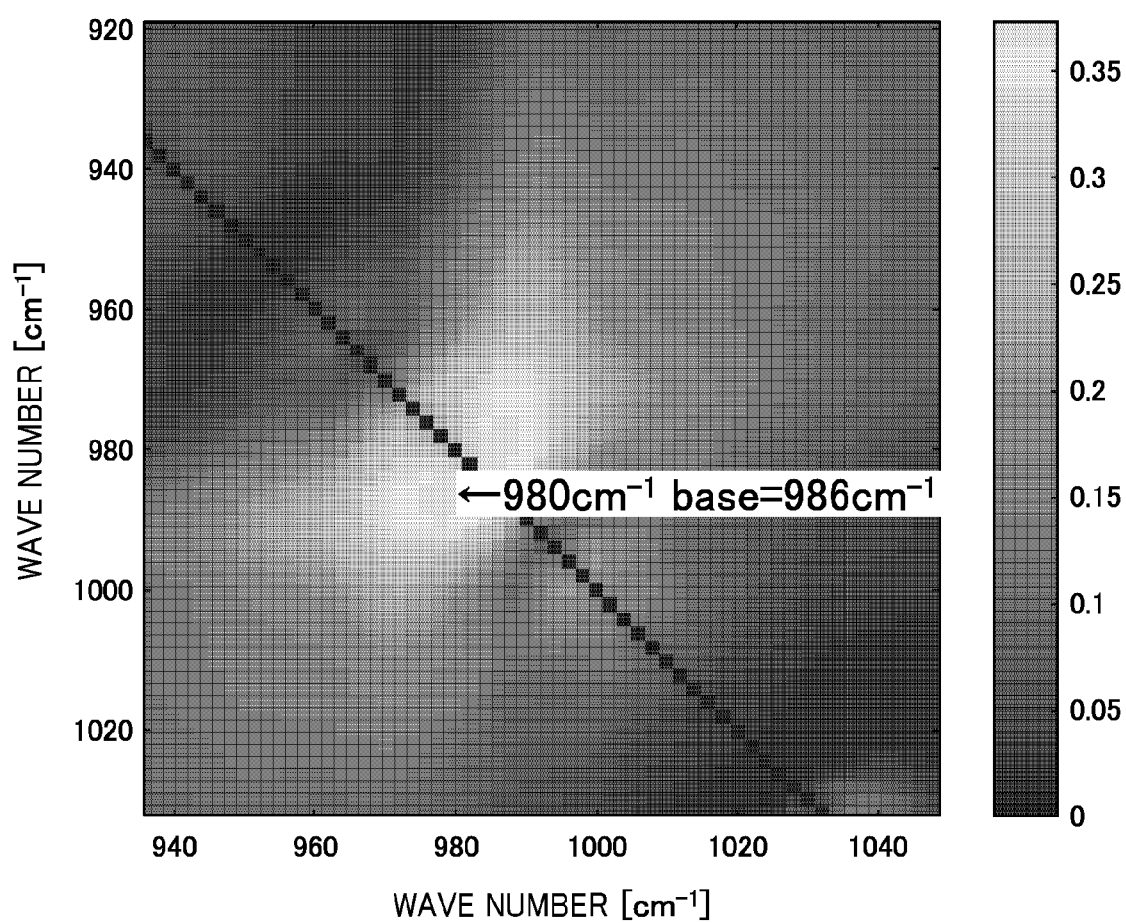
FIG. 8 is an enlarged view of a region A.

FIG. 8 is an enlarged view of a region A.

For the first wavelength (e.g., the sense wavelength) in the range of from 950 $cm^{-1}$ or more and 990 $cm^{-1}$ or less, the coefficient of determination for a wave number of 980 $cm^{-1}$ is particularly large. For the second wavelength (e.g., the base wavelength) in the range of from 970 $cm^{-1}$ or more and 1010 $cm^{-1}$ or less, the coefficient of determination for a wave number of 986 $cm^{-1}$ is particularly large.

Even in a case where multiple people with different contents of the meal undergo the measurement at any desired timing during a period from 100 minutes before eating to 250 minutes after eating, the blood glucose level can be accurately estimated by selecting the first wavelength in the range of from 950 $cm^{-1}$ or more to 990 $cm^{-1}$ or less and selecting the second wavelength in the range of from 970 $cm^{-1}$ or more to 1010 $cm^{-1}$ or less.

A stable and accurate measurement over a period from before eating to after eating is achieved by using two or more wavelengths selected from the above-described ranges and estimating the blood glucose level based on the absorbance for each wavelength using the prediction formula (2).

Using the absorbance ratio obtained by dividing the absorbance at the sense wavelength by the absorbance at the base wavelength serving as a reference enables a correction of variations in the contact state of the lips and the ATR prism, which varies for each measurement.

Figure 9:
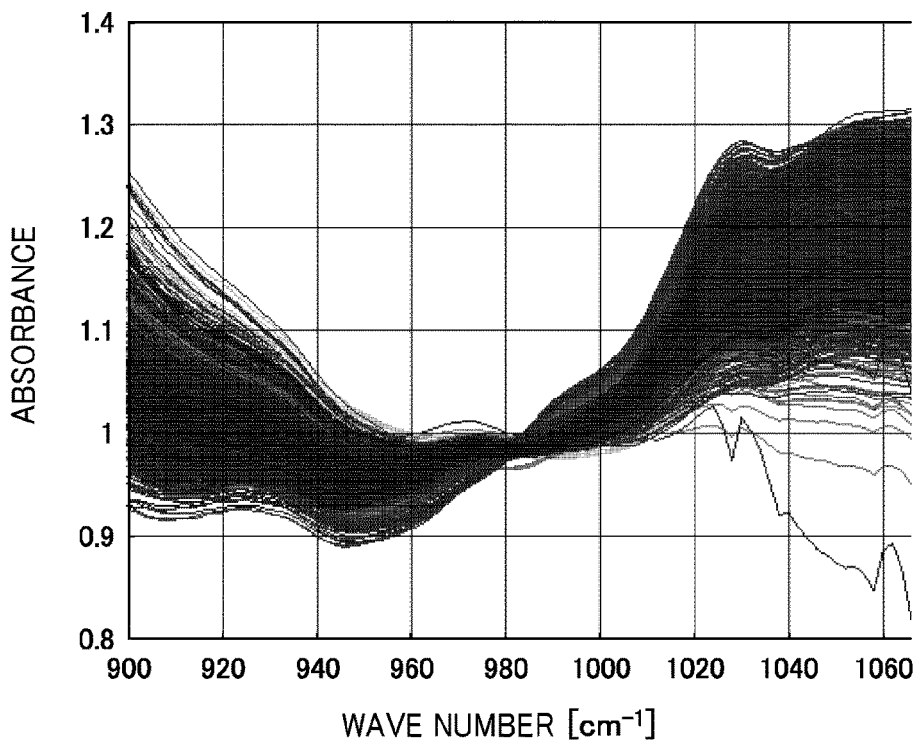
FIG. 9 is a diagram in which absorbances for datasets obtained at wavenumbers around 990 $cm^{-1}$ are overwritten.

FIG. 9 is an overlay of absorbances obtained by rendering data obtained at the sense wavelength around 990 $cm^{-1}$ normalized by the base wavelength near the sense wavelength.

Although normalized absorbances vary depending on data, a small peak of absorbances at wavelengths around 990 $cm^{-1}$ is observed when viewed as a whole. This peak is an absorption peak due to the $CH_2OH$ group of glucose.

As illustrated in the region A of the determination-coefficient map in FIG. 7, a combination of the sense wavelength selected from the range of from 950 $cm^{-1}$ or more to 990 $cm^{-1}$ or less and the base wavelengths selected from the range of from 970 $cm^{-1}$ or more to 1010 $cm^{-1}$ or less, or a reverse combination thereof is suitable for detection of glucose.

The first wavelength selected from the range of from 950 $cm^{-1}$ or more to 990 $cm^{-1}$ or less and the second wavelength selected from the range of from 970 $cm^{-1}$ or more to 1010 $cm^{-1}$ or less are set to the light source device 11 of the measuring apparatus 1 in FIG. 1 to measure a blood glucose level. This achieves stable and accurate non-invasive blood glucose measurement regardless of individual differences and fluctuations in the contact state of the measurement optical element 17 and the measurement site.

Notably, the wavelengths used for measurement of biomarkers are not limited to one sense wavelength and one base wavelength. For example, in addition to the sense wavelength and the base wavelength described above, a second base wavelength is selected from the range of from 950 $cm^{-1}$ or more to 990 $cm^{-1}$ or less, or the range of from 970 $cm^{-1}$ or more and 1010 $cm^{-1}$ or less. For another example, in addition to the sense wavelength and the base wavelength described above, two or more wavelengths, for example, about 5 wavelengths or 20 wavelengths, are used in a range of from 950 $cm^{-1}$ or more to 1010 $cm^{-1}$ or less to reduce noise at the time of measurement by averaging these wavelengths. Alternatively, the second base wavelength is selected from the region B or the region C.

The absorbance is defined as a function of the base wavelength to have the ratio of the absorbance at the first base wavelength to the absorbance at the second base wavelength being 1. For example, when the horizontal axis represents the base wavelength, and the vertical axis represents the absorbance at the base wavelength, the intercept is determined to have a slope of the straight line (i.e., a normalized straight line) being 1. The absorbance obtained at the sense wavelength is divided by the absorbance at the base wavelength represented by this linear equation to estimate the blood glucose level using the prediction formula (2).

For example, a wave number of 954 $cm^{-1}$ is set as the first base wavelength, a wave number of 1202 $cm^{-1}$ is set as the second base wavelength, and the absorption of the sense wave length is divided by the linear expression of the absorption of the base wave length.

Figure 10:
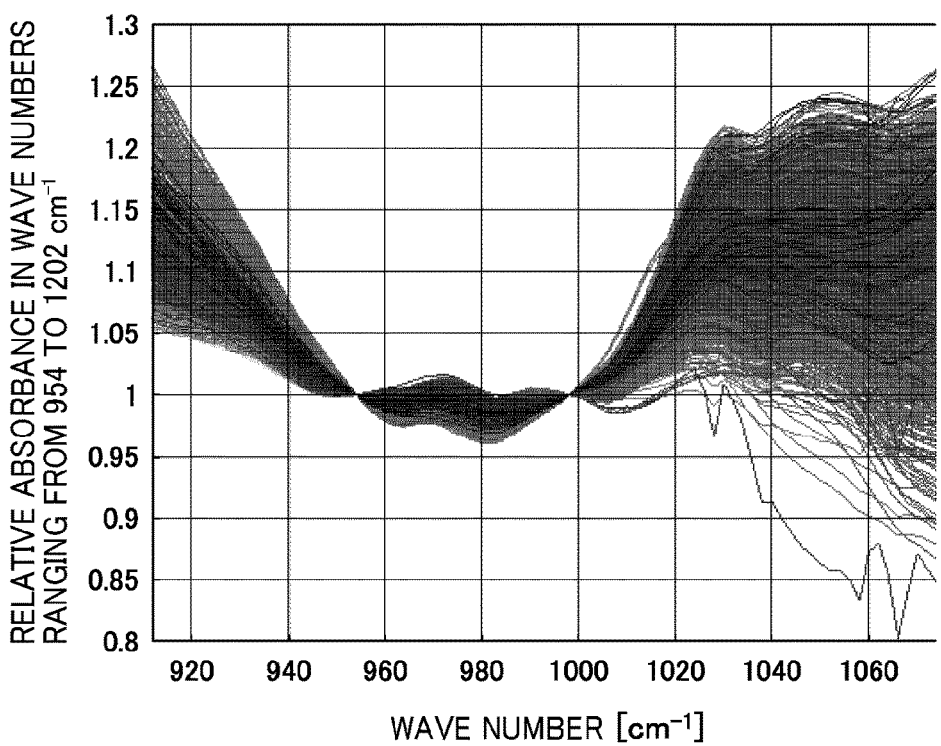
FIG. 10 is a diagram in which absorbances obtained from one sense wavelength and two base wavelengths are overwritten.

FIG. 10 is a diagram in which absorbances obtained from one sense wavelength and two base wavelengths are overwritten. The two base wavelengths are 954 $cm^{-1}$ and 1202 $cm^{-1}$, and the sense wavelength is 992 $cm^{-1}$. As illustrated in FIG. 10, the peak of $CH_2OH$ in the wavelengths near 990

$cm^{-1}$ can be extracted, and thus an appropriate blood glucose level can be predicted. Using such three wavelengths increases the coefficient of determination as compared to the measurement using two wavelengths.

Instead of setting the sense wavelength and the base wavelength to specific wavelengths, an average of a series of wavelengths included in the above-described wavelength range is used for at least one of the sense wavelength and the base wavelength. For example, an average value of absorbances measured at wavelengths between 992 $cm^{-1}$ and 994 $cm^{-1}$ is used as the absorbance at the sense wavelength. Thus, measurement noise can be reduced. Alternatively, in addition to the sense wavelength and the base wavelength of specific wavelengths, an average value of absorbances at the wavelengths within a given range is used.

In some examples, a wavelength selected from the region B or the region C is used as the third wavelength. For example, in addition to the predicted values at the sense wavelengths and the base wavelengths selected from the region A, an average value of the predicted values at wavelengths of from 1700 $cm^{-1}$ to 1760 $cm^{-1}$ is combined to obtain a final predicted value. In this case, the blood glucose level is predicted from multiple viewpoints, and the estimation accuracy is improved.

Figure 11:
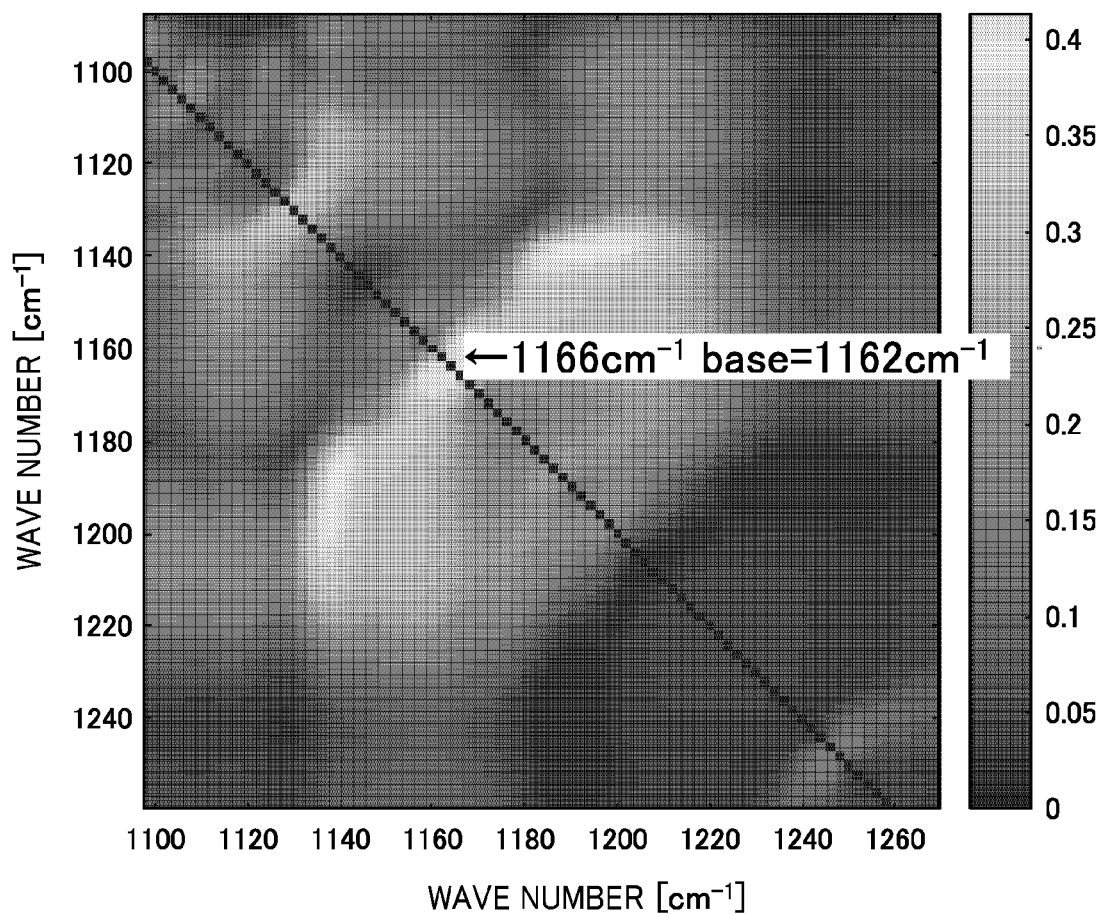
FIG. 11 is an enlarged view of a region B.

FIG. 11 is an enlarged view of the region B.

In the region B, both the sense wavelength and the base wavelength have large coefficients of determination in the range of the wavelength (wave number) of from 1130 $cm^{-1}$ to 1220 $cm^{-1}$. It can be found that the region B includes combinations of the sense wavelength and the base wavelength in which the coefficient of determination is particularly high.

One combination (the first combination) is observed as a region in the vicinity of the oblique straight line in FIG. 11. In this case, one of the base wavelength and the sense wavelength is a first wavelength, and the other one is a second wavelength: the first wavelength is in the range of from 1156 $cm^{-1}$ to 1164 $cm^{-1}$; and the second wavelength is in the range of from 1164 $cm^{-1}$ to 1174 $cm^{-1}$. With such a combination, the coefficient of determination becomes high.

Figure 12:
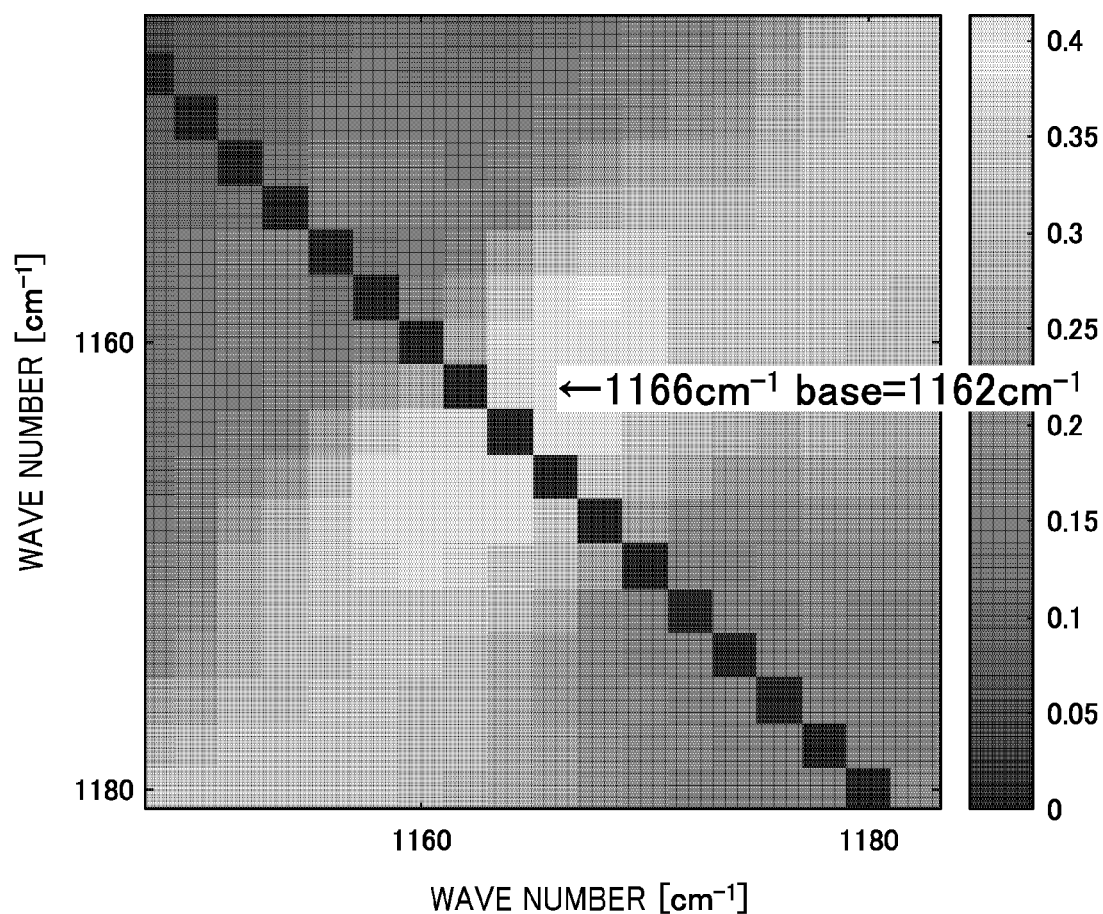
FIG. 12 is an enlarged view of a first mapping range in the region B.

FIG. 12 is an enlarged view of an area in and around the range of such a combination.

Another combination (the second combination) is observed as a vertically long area extending downward from the oblique straight line in FIG. 11 or a horizontally long area extending upward from the oblique straight line. In this case, one of the base wavelength and the sense wavelength is a first wavelength, and the other one is a second wavelength: the first wavelength is in the range of from 1134 $cm^{-1}$ to 1146 $cm^{-1}$; and the second wavelength is in the range of from 1170 $cm^{-1}$ to 1216 $cm^{-1}$. With such a combination, the coefficient of determination becomes high.

Figure 13:
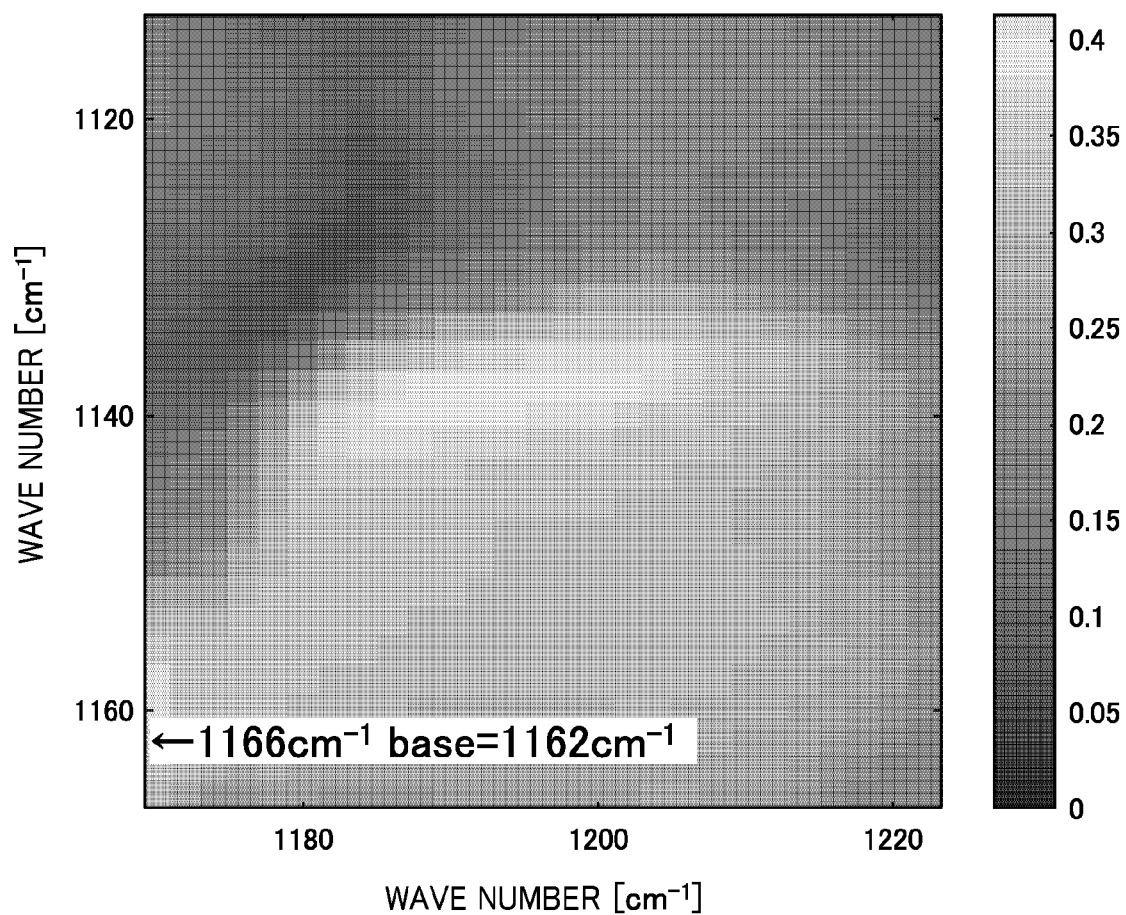
FIG. 13 is an enlarged view of a second mapping range in the region B.

FIG. 13 is an enlarged view of an area in and around the range of the second combination. FIG. 13 indicates a high correlation between the measurement results and the typical transition of the blood glucose level, which is achieved by using the base wavelength in the range of from 1170 $cm^{-1}$ to 1216 $cm^{-1}$ and the sense wavelength in the range of from 1134 $cm^{-1}$ to 1146 $cm^{-1}$.

Even in a case where multiple people with different contents of the meal undergo the measurement at any desired timing during a period from 100 minutes before eating to 250 minutes after eating, the blood glucose level can be accurately estimated by selecting the first combination or the second combination of the sense wavelength and the base wavelength.

A stable and accurate measurement over a period from before eating to after eating is achieved by using two or more wavelengths selected from the region B and estimating the blood glucose level based on the absorbance for each wavelength using the prediction formula (2). Using the absorbance ratio obtained by dividing the absorbance at the sense wavelength by the absorbance at the base wavelength serving as a reference enables a correction of variations in the contact state of the lips and the ATR prism, which varies for each measurement.

Figure 14:
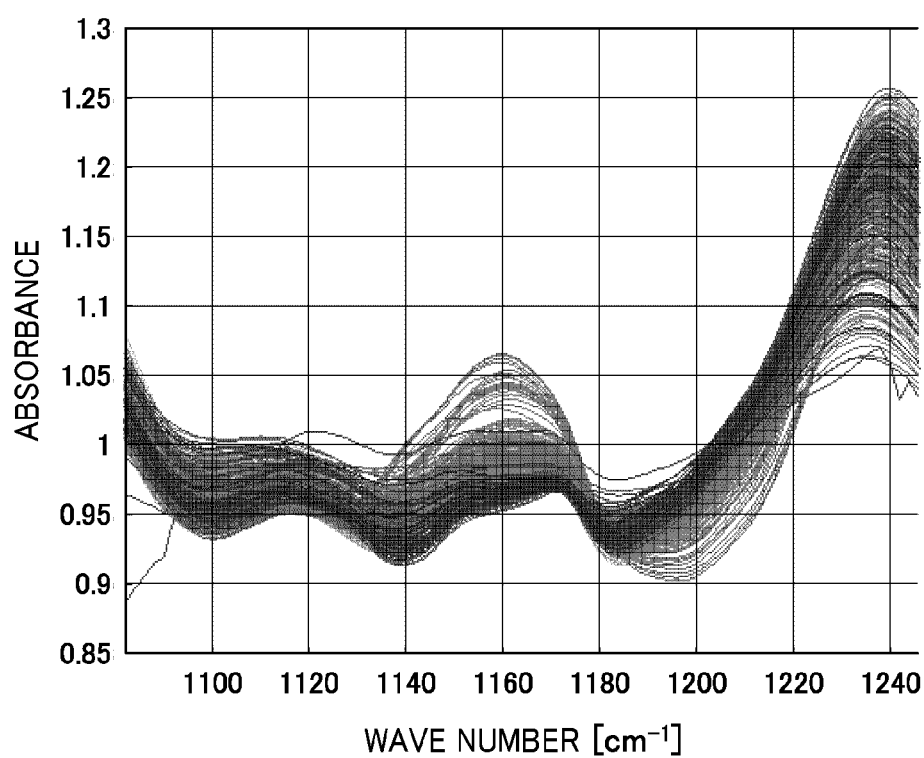
FIG. 14 is a graph in which absorbances for datasets obtained at wavenumbers around 1160 $cm^{-1}$ are overwritten.

FIG. 14 is an overlay of absorbances obtained by rendering data obtained at the sense wavelength near 1160 $cm^{-1}$ normalized by the base wavelength near the sense wavelength. Although normalized absorbances vary depending on data, a peak of an absorbance at a wavelength around 1160 $cm^{-1}$ is observed. This peak is an absorption peak due to the pyranose ring of glucose. As illustrated in the determination-coefficient map in FIG. 11, two wavelengths selected from the range of from 1130 $cm^{-1}$ or more to 1170 $cm^{-1}$ or less is suitable for detection of glucose.

The first wavelength and the second wavelength selected from the range of from 1130 $cm^{-1}$ or more to 1220 $cm^{-1}$ or less are set to the light source device 11 of the measuring apparatus 1 in FIG. 1 to measure a blood glucose level. This achieves stable and accurate non-invasive blood glucose measurement regardless of individual differences and fluctuations in the contact state of the measurement optical element 17 and the measurement site.

Notably, the wavelengths used for measurement of biomarkers are not limited to one sense wavelength and one base wavelength. For example, in addition to the sense wavelength and the base wavelength (i.e., a first wavelength and a second wavelength) selected from the range of from 1130 $cm^{-1}$ or more to 1220 $cm^{-1}$ or less, a second base wavelength (i.e., a third wavelength) is used. The second base wavelength is selected from the range of from 1130 $cm^{-1}$ or more to 1220 $cm^{-1}$ or less; from the region A in the range of from 950 $cm^{-1}$ or more to 1010 $cm^{-1}$ or less; or from the region C in the range of from 1700 $cm^{-1}$ or more to 1760 $cm^{-1}$ or less.

For the second base wavelength, the absorbance is defined as a function of the base wavelength to have the ratio of the absorbance at the first base wavelength to the absorbance at the second base wavelength being 1. In other words, a normalized line is determined such that the ratio of the absorbance (i.e., the second absorbance) at the first base wavelength (i.e., the second wavelength) to the absorbance (i.e., the third absorbance) at the second base wavelength (i.e., the third wavelength) becomes 1. For example, when the horizontal axis represents the base wavelength, and the vertical axis represents the absorbance at the base wavelength, the intercept is determined to have a slope of the straight line being 1. The absorbance obtained at the sense wavelength is divided by the absorbance at the base wavelength represented by this linear equation to estimate the blood glucose level using the prediction formula (2). Using such three wavelengths increases the coefficient of determination as compared to the measurement using two wavelengths.

Instead of setting the sense wavelength and the base wavelength to specific wavelengths, an average of absorbances of a series of wavelengths included in the region B is used for at least one of the sense wavelength and the base wavelength. Alternatively, in addition to the sense wavelength and the base wavelength of specific wavelengths, an average value of absorbances at the wavelengths within a given range is used. For example, an average value of absorbances at wavelengths of from 1162 cm$^{-1}$ to 1168 cm$^{-1}$ having a high coefficient of determination is used as the absorbance of at least one of the sense wavelength and the base wavelength or as the third absorbance. Thus, measurement noise can be reduced. In this case, the blood glucose level is predicted from multiple viewpoints (e.g., glucose components), and the estimation accuracy is improved.

Figure 15:
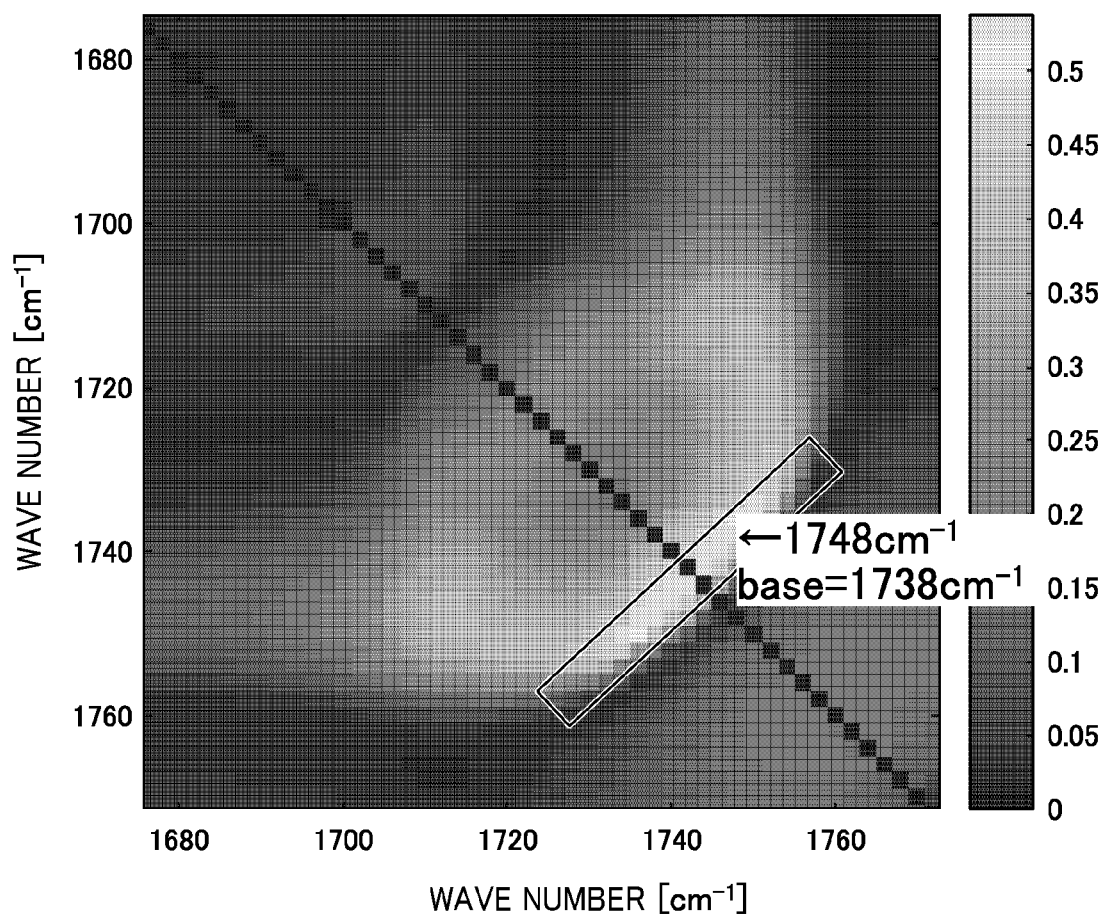
FIG. 15 is an enlarged view of a region C.

FIG. 15 is an enlarged view of the region C.

In the region C, both the sense wavelength and the base wavelength have large coefficients of determination in the range of the wavelength (wave number) of from 1700 cm$^{-1}$ to 1760 cm$^{-1}$. In this case, one of the base wavelength and the sense wavelength is a first wavelength, and the other one is a second wavelength: the first wavelength is 1738±8 cm$^{-1}$; and the second wavelength is 1748±8 cm$^{-1}$. With such a combination, the coefficient of determination becomes particularly high.

Both the sense wavelength and base wavelength are selected from the range of 1743±8 cm$^{-1}$.

When the first wavelength is wave 1, and the second wavelength is wave 2, a particularly bright range (a range with a large coefficient of determination) surrounded by a frame in FIG. 15 is given by:

$$\text{Wave 2}=1743\text{ cm}^{-1}-(\text{wave 1}-1743\text{ cm}^{-1})\pm 8\text{ cm}^{-1}$$

Figure 16:
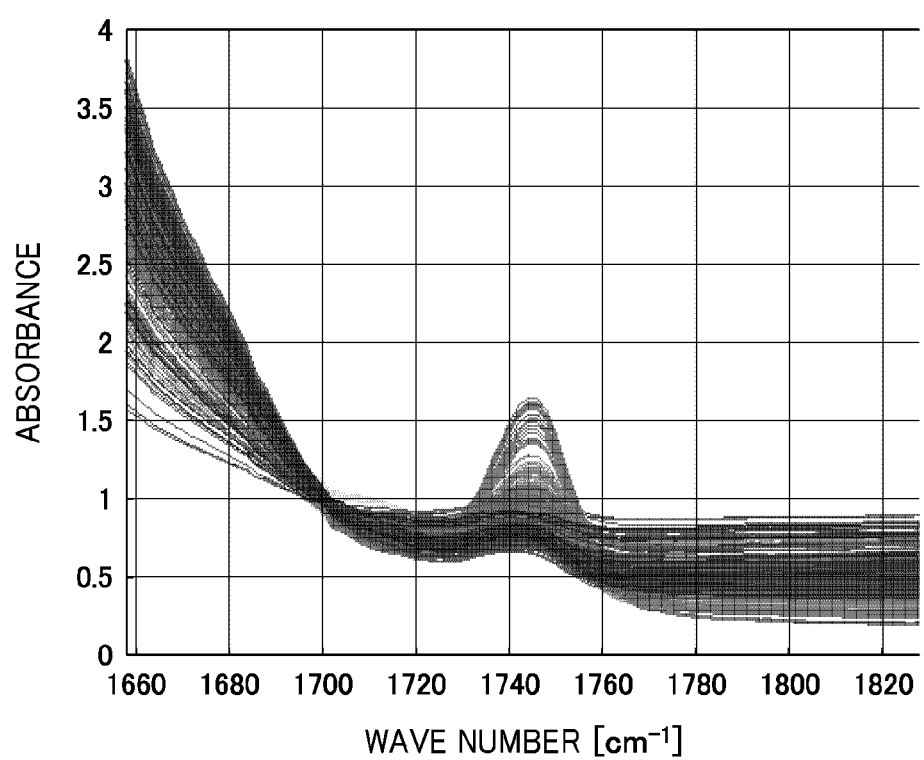
FIG. 16 is a diagram in which absorbances for datasets obtained at wavenumbers around 1740 $cm^{-1}$ are overwritten.

FIG. 16 is an overlay of absorbances obtained by rendering data obtained at the sense wavelength near 1740 cm$^{-1}$ normalized by the base wavelength near the sense wavelength. An absorbance peak is observed in the wavelengths of from 1741 cm$^{-1}$ to 1744 cm$^{-1}$. At wavelengths of around 1740 cm$^{-1}$, an absorption peak of carbonyl groups due to C=O bonds is observed. By detecting substances related to intracellular glucose metabolism such as ketone bodies such as acetoacetic acid and 3-hydroxybutyric acid, and G6P, F6P, pyruvate, and intracellular acetyl CoA (coenzyme A) present in the cytosol of cells, the blood glucose level can be estimated by regression.

In some examples, a wavelength selected from the region C is combined with a wavelength selected from the region A or a wavelength selected from the region B. Thus, the blood sugar level is estimated from various components in the blood, and the measurement accuracy is improved.

In the embodiments described above, two wavelengths are used to estimate the blood glucose level. In order to further improve the estimation accuracy, the blood glucose level is estimated based on the cross-correlation between the absorption spectrum of the glucose aqueous solution and the absorption spectrum of the measurement target. A large cross-correlation between the absorption spectrum of the glucose aqueous solution and the absorption spectrum of the measurement target indicates that a large amount of glucose is contained in the measured absorption spectrum of a subject that has undergone the measurement.

Differences or variations in the contact state of the subject and the ATR prism are cross-corrected to capture a minute change, so as to estimate the blood glucose level based on the cross-correlation values. For example, the absorption spectrum of the glucose aqueous solution and the absorption spectrum of the measurement target are preprocessed and normalized before the cross-correlation is obtained. The absorption spectrum of glucose (a substance to be measured) is measured in advance and stored in a memory inside or outside the information processing device 30. In some examples, the preprocessing is performed by the data processing unit 31 of the information processing device 30. The preprocessing is divided into three stages as an example.

First, the absorption spectrum of the glucose aqueous solution and the absorption spectrum of the measurement target each are divided by an absorbance of a neighboring wave number.

The output absorbance_d(i) of the divided spectrum is given by formula (3) below:

$$\text{absorbance\_}d(i)=[\text{absorbance}(i)/\text{absorbance}(i-r1)]-1 \quad (3)$$

where the character "absorbance (i)" is an absorption at a wave number i, and the sign "r1" is a value that indicates a difference from a wave number used for normalization. When the absorbance (i) and the absorbance (i−r1) have the same value, the output of the divided spectrum is 0.

Next, a neighboring wave number is subtracted from the divided value to capture a small change. The output absorbance_d2(i) of the differential spectrum is given by formula (4) below:

$$\text{absorbance\_}d2(i)=\text{absorbance\_}d(i)-\text{absorbance\_}d(i-r2) \quad (4)$$

where the sign "r2" is a value that indicates a difference from a wave form used for subtraction.

Further, smoothing is performed by applying a moving average filter to the output of the differential spectrum to reduce variations in data. The spectrum abs(i) after the application of the moving average filter is given by $$\text{abs}(i) = \frac{1}{N} \sum_{n=i-N/2}^{i+N/2} \text{absorbance\_}d2(n)$$

where N is the range in which the moving average filter is averaged.

When "ref" is the absorption spectrum of the glucose aqueous solution that has been preprocessed, and "abs" is the absorption spectrum of the measurement target, which has been preprocessed, the cross-correlation is given by $$\text{corr} = \sum_{n=st}^{en} ref(n) * \text{abs}(n)$$

where "corr" is a cross-correlation value, "st" is a beginning wavelength in the wavelength range in which the cross-correlation is obtained, and "en" is the final wavelength of the wavelength range in which the cross-correlation is obtained.

The target biomarker is obtained by linearly converting the cross-correlation value "corr" using formula (5) below, and in this example, the estimation amount "estimated_glucose" of the blood glucose level is obtained:

$$\text{Estimated\_glucose}=a\times(\text{corr})+b \quad (5)$$

where "a" and "b" are coefficients obtained by fitting using data with label information of the true blood glucose level.

This method enables estimation of a blood glucose level from the absorption spectrum of the measurement target. However, depending on the wavelength range, there might be a case where no clue such as an absorption peak or dip in the spectrum of the glucose aqueous solution is obtained, or a case where a peak or dip of a substance that fluctuates in addition to glucose is included, which might hinder estimation. In view of such situations, an appropriate wavelength range is to be used.

Figure 17:
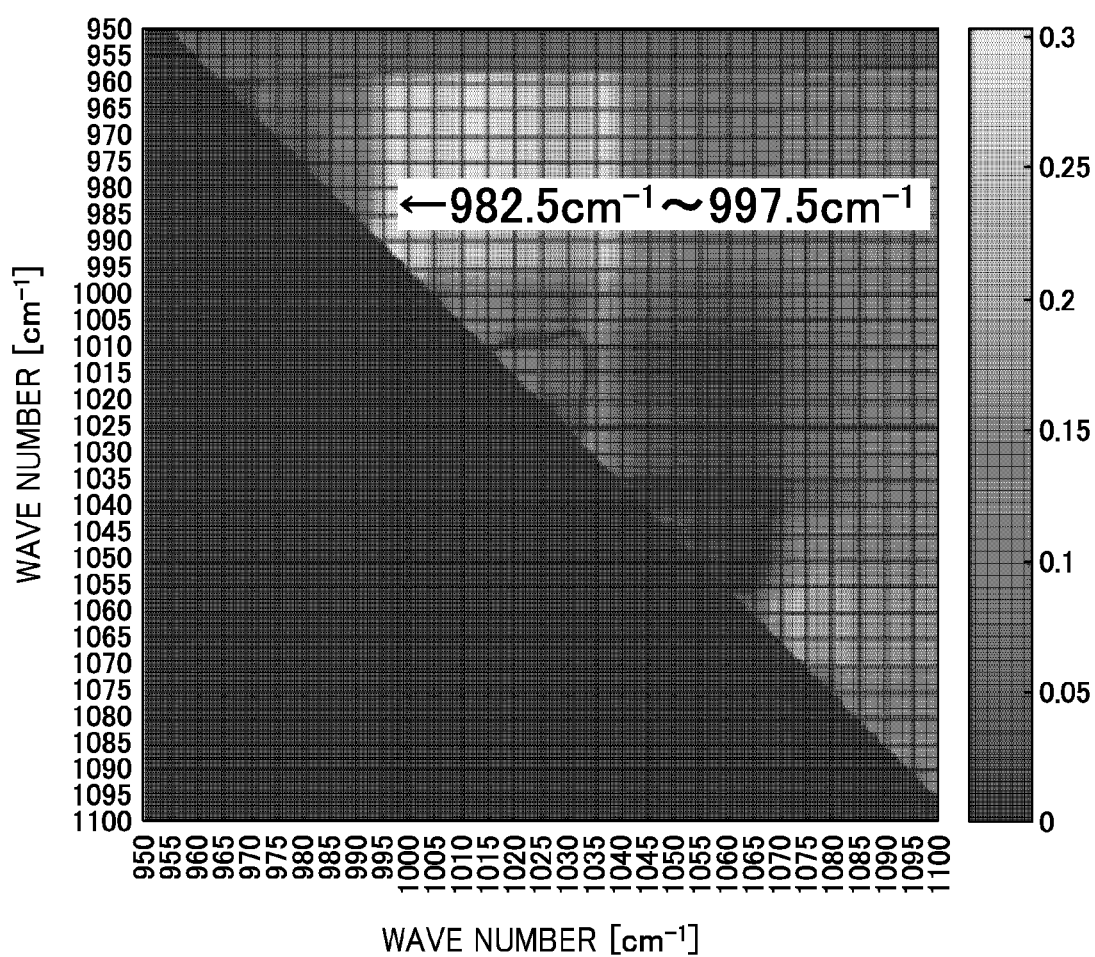
FIG. 17 is a graph of a range in which an estimated blood glucose level change is highly correlated with a typical blood glucose level change of a human.

FIG. 17 is a graph of a range in which a blood glucose level change estimated from the cross-correlation is highly correlated with a typical blood glucose level change of a human. For an absorption spectrum of a measurement target measured at each predetermined time after eating, a correlation coefficient between an estimated amount of a blood glucose level (estimated_glucose) obtained from a cross-correlation value and a typical blood glucose level change of a human after eating is indicated by a light and shade indicator. The vertical axis represents the beginning wavelength "st", and the horizontal axis represents the final wavelength "en".

FIG. 17 indicates an area with a good correlation (i.e., a bright area). The highest correlation is obtained with the combination of st of 982.5 $cm^{-1}$ and en of 997.5 $cm^{-1}$. The absorption of the $CH_2OH$ group of glucose seems to be measured in this wavelength range. This wavelength range exhibits the results coincident with the results of the wavelength range (A) that is suitable for the above-described measurement.

In the wavelength range (A), the light having the first wavelength selected from the range of the wave number of from 970 $cm^{-1}$ or more to 1010 $cm^{-1}$ or less and the light having the second wavelength selected from the range of the wave number of from 950 $cm^{-1}$ or more to 990 $cm^{-1}$ or less are used, which suggests that a high correlation is obtained by estimation using the cross-correlation value. Using these wavelength ranges enables an accurate estimation of the blood glucose level. This estimation method can be applied not only to estimation of a human but also to estimation of a blood glucose level of an animal or other substances in the body.

Although the wavelength selection has been described by taking the measurement of the blood glucose level as an example, the non-invasive measurement according to the embodiments of the present disclosure is not limited to measurement of the blood glucose level. The technical idea of selecting and determining a wavelength according to at least one embodiment can also be applied to measurement of other biomarkers such as proteins and tumor DNA in blood.

As described above, when the third wavelength or fourth wavelength is selected in addition to the two wavelengths, the region A, the region B, and the region C are combined with each other. This enables a stable and accurate measurement of a biomarker regardless of individual differences or differences in measurement environments.

The above-described embodiments are illustrative and do not limit the present invention. Thus, numerous additional modifications and variations are possible in light of the above teachings. For example, elements and/or features of different illustrative embodiments may be combined with each other and/or substituted for each other within the scope of the present invention.

The present invention can be implemented in any convenient form, for example using dedicated hardware, or a mixture of dedicated hardware and software. The present invention may be implemented as computer software implemented by one or more networked processing apparatuses. The processing apparatuses include any suitably programmed apparatuses such as a general purpose computer, a personal digital assistant, a Wireless Application Protocol (WAP) or third-generation (3G)-compliant mobile telephone, and so on. Since the present invention can be implemented as software, each and every aspect of the present invention thus encompasses computer software implementable on a programmable device. The computer software can be provided to the programmable device using any conventional carrier medium (carrier means). The carrier medium includes a transient carrier medium such as an electrical, optical, microwave, acoustic or radio frequency signal carrying the computer code. An example of such a transient medium is a Transmission Control Protocol/Internet Protocol (TCP/IP) signal carrying computer code over an IP network, such as the Internet. The carrier medium also includes a storage medium for storing processor readable code such as a floppy disk, a hard disk, a compact disc read-only memory (CD-ROM), a magnetic tape device, or a solid state memory device.

Each of the functions of the described embodiments may be implemented by one or more processing circuits or circuitry. Processing circuitry includes a programmed processor, as a processor includes circuitry. A processing circuit also includes devices such as an application specific integrated circuit (ASIC), a digital signal processor (DSP), a field programmable gate array (FPGA), and conventional circuit components arranged to perform the recited functions.

This patent application is based on and claims priority to Japanese Patent Application No. 2020-129357, filed on Jul. 30, 2020 and Japanese Patent Application No. 2021-093778, filed on Jun. 3, 2021, in the Japan Patent Office, the entire disclosures of which are hereby incorporated by reference herein.

REFERENCE SIGNS LIST

1 Measuring apparatus
10 Measurement optical system
11 Light source device
111, 112, 113 Light sources
12 Switch
121, 122, 123 Switching element
13, 14 Optical multiplexer/demultiplexer
15 and 16 Light guide member
17 Measurement optical element
18 Photosensor
25 Data logger
30 Information processing device
31 Data processing unit
32 Biomarker estimation unit
33 Switching control unit
34 Timing control unit

The invention claimed is:

1. A measuring apparatus, comprising:
a light source to emit light in a mid-infrared region, the light including:
first-wavelength light having a wave number of from 970 cm-1 or more to 1010 cm-1 or less; and
second-wavelength light different from the first-wavelength light, the second-wavelength light having a wave number of from 950 cm-1 or more to 990 cm-1 or less;
a photosensor to detect the light emitted from the light source and reflected by a measurement target; and
information processing circuitry configured to:
obtain a first absorbance of the first-wavelength light and a second absorbance of the second-wavelength light from an output of the photosensor; and
determine a biomarker of the measurement target based on the first absorbance and the second absorbance.

2. A measuring apparatus comprising:
a light source to emit light in a mid-infrared region, the light including first-wavelength light and second-wavelength light different from the first-wavelength light, each having a wave number of from 1130 cm-1 or more to 1220 cm-1 or less;

a photosensor to detect the light emitted from the light source and reflected by a measurement target; and an information processing circuitry configured to:

obtain a first absorbance of the first-wavelength light and a second absorbance of the second-wavelength light from an output of the photosensor; and determine a biomarker of the measurement target based on the obtained first absorbance and the second absorbance.

3. The measuring apparatus according to claim 2,
wherein the first—wavelength light has a wave number ranging from 1156 cm-1 or more to 1164 cm-1 or less, and the second—wavelength light has a wave number ranging from 1164 cm-1 or more to 1174 cm-1 or less.

4. The measuring apparatus according to claim 2,
wherein the first—wavelength light has a wave number ranging from 1134 cm-1 or more to 1146 cm-1 or less, and the second—wavelength light has a wave number ranging from 1170 cm-1 or more to 1216 cm-1 or less.

5. The measuring apparatus according to claim 1,
wherein the information processing circuitry is configured to:
divide the first absorbance by the second absorbance to obtain a value; and
estimate the biomarker based on the value.

6. The measuring apparatus according to claim 1,
wherein the light further includes third—wavelength light having a wave number of from 1700 cm-1 or more to 1760 cm-1 or less, and
wherein the information processing circuitry is configured to determine the biomarker based on the first absorbance, the second absorbance, and a third absorbance of the third—wavelength light.

7. The measuring apparatus according to claim 1,
wherein the light further includes third—wavelength light having a wave number of from 1130 cm-1 or more to 1220 cm-1 or less, and
wherein the information processing circuitry is configured to determine the biomarker based on the first absorbance, the second absorbance, and a third absorbance of the third—wavelength light.

8. The measuring apparatus according to claim 2,
wherein the light further includes third—wavelength light having a wave number of from 970 cm-1 or more to 1010 cm-1 or less or from 950 cm-1 or more to 990 cm-1 or less, and
wherein the information processing circuitry is configured to determine the biomarker based on the first absorbance, the second absorbance, and a third absorbance of the third—wavelength light.

9. The measuring apparatus according to claim 6,
wherein the information processing circuitry is configured to:
determine a normalized line to have a ratio of the second absorbance to the third absorbance being 1; and
normalize the first absorbance using the normalized line.

10. The measuring apparatus according to claim 1,
wherein the information processing circuitry is further configured to:
obtain a cross—correlation value from a preliminarily—acquired absorption spectrum of a substance to be measured within the measurement target and an absorption spectrum of the measurement target acquired from the output of the photosensor; and
estimate the biomarker of the measurement target based on the cross—correlation value.

11. The measuring apparatus according to claim 1, further comprising—
a measurement optical structure between the light source and the photosensor, the measurement optical structure to emit light reflected by the measurement target, to the photosensor.

12. The measuring apparatus according to claim 11,
wherein the measurement optical structure element is an attenuated total reflection prism.

13. The measuring apparatus according to claim 2,
wherein the information processing circuitry is configured to:
divide the first absorbance by the second absorbance to obtain a value; and
estimate the biomarker based on the value.

14. The measuring apparatus according to claim 2,
wherein the light further includes third—wavelength light having a wave number of from 1700 cm-1 or more to 1760 cm-1 or less, and
wherein the information processing circuitry is configured to determine the biomarker based on the first absorbance, the second absorbance, and a third absorbance of the third—wavelength light.

15. The measuring apparatus according to claim 14,
wherein the information processing circuitry is configured to:
determine a normalized line to have a ratio of the second absorbance to the third absorbance being 1; and
normalize the first absorbance using the normalized line.

16. The measuring apparatus according to claim 2,
wherein the information processing circuitry is further configured to:
obtain a cross—correlation value from a preliminarily—acquired absorption spectrum of a substance to be measured within the measurement target and an absorption spectrum of the measurement target acquired from the output of the photosensor; and
estimate the biomarker of the measurement target based on the cross—correlation value.

17. The measuring apparatus according to claim 2, further comprising:
a measurement optical structure between the light source and the photosensor, the measurement optical structure to emit light reflected by the measurement target, to the photosensor.

18. The measuring apparatus according to claim 17,
wherein the measurement optical structure is an attenuated total reflection prism.

* * * * *